United States Patent [19]

Müller et al.

[11] Patent Number: 5,306,503

[45] Date of Patent: Apr. 26, 1994

[54] PATCH WITH A HIGH CONTENT OF SOFTENING INGREDIENTS

[75] Inventors: Walter Müller, Neuwied; Raphaela Minderop, Munich; Andreas Teubner, Pfaffenhofen, all of Fed. Rep. of Germany

[73] Assignee: LTS Lohmann Therapie-Systeme GmbH & Co. KG, Neuwied, Fed. Rep. of Germany

[21] Appl. No.: 718,668

[22] Filed: Jun. 21, 1991

[30] Foreign Application Priority Data

Jun. 25, 1990 [DE] Fed. Rep. of Germany ....... 4020144

[51] Int. Cl.$^5$ ............................................. A61K 13/00
[52] U.S. Cl. .................... 424/449; 424/447; 424/448
[58] Field of Search .................. 424/449, 448, 447

[56] References Cited

U.S. PATENT DOCUMENTS

| | | | |
|---|---|---|---|
| 4,859,696 | 8/1989 | Kamiya et al. | 424/449 |
| 4,948,588 | 8/1990 | Kamiya et al. | 424/449 |
| 4,956,181 | 9/1990 | Bayer et al. | 424/448 |
| 4,994,267 | 2/1991 | Sablotsky | 424/449 |
| 5,089,267 | 2/1992 | Hille et al. | 424/449 |
| 5,132,115 | 7/1992 | Wolter et al. | 424/449 |

FOREIGN PATENT DOCUMENTS

| | | |
|---|---|---|
| 0305758 | 8/1988 | European Pat. Off. . |
| 0379933 | 1/1990 | European Pat. Off. . |
| 3843238 | 12/1988 | Fed. Rep. of Germany . |
| 3843239 | 12/1988 | Fed. Rep. of Germany . |

*Primary Examiner*—Thurman K. Page
*Assistant Examiner*—William E. Benston
*Attorney, Agent, or Firm*—Sprung Horn Kramer & Woods

[57] ABSTRACT

The present invention relates to a device for the topical and systemic administration of active substances to or through the skin consisting of a backing layer, at least one self-adhesive layer, and a removable protective layer, wherein the self-adhesive layer consists of (a) 100 parts by weight of a polyacrylate adhesive,
(b) 5 to 150, preferably 10 to 100, and in particular 15 to 50 parts by weight of a film former compatible with polyacrylates,
(c) 0 to 250 parts by weight of a non-softening active substance and/or adjuvant, and
(d) 10 to 250 parts by weight of a softening active substance and/or adjuvant.

34 Claims, No Drawings

PATCH WITH A HIGH CONTENT OF SOFTENING INGREDIENTS

The present invention relates to a device for the topical and systemic administration of active substances to or through the skin.

Dermal and transdermal therapeutic systems have become a wide-spread form of administering drugs. In their most simple form, they consist of a backing layer, a self-adhesive, active substance-containing matrix, and a removable protective layer. In addition to the active substance/s and adjuvant/s, the matrix layer of these so-called matrix systems preferably consists of a self-adhesive polymer or a self-adhesive polymeric mixture, respectively. Such a system is described, e.g., by U.S. Pat. No. 3,734,097.

The tackiness of the matrix is of particular importance in these systems—only a safe and reproducible contact of the system to the skin ensures that the active substance can be transferred to or into the skin in the desired manner through diffusion processes; it may then optionally pass the skin and become systemically effective.

If a resin of polyacrylate or polysiloxane is used as adhesive matrix component, the tackiness is determined, amongst others, by the mean molecular weight and the molecular weight distribution of the resin. In case of glues containing as basic polymer a non-adhesive, rubber-like polyisobutylene or a styrene-butadienenblock copolymer, additional tackifying resins have to be admixed. Frequently, these are chemically modified natural resins.

In many cases very high active substance concentrations have to be used to achieve sufficiently high active substance flows from the systems to and through the skin. In particular, if these active substances are liquid at room temperature, they have negative effects on the properties of the matrix. Cohesion lessens, and the consistency of the matrix resembles honey or "flies glue".

Similar problems occur in case of active substances which either can only hardly penetrate the barrier of the human skin at a sufficient amount and velocity due to their chemics-physical properties, or have to be administered at relatively high therapeutic doses.

In these cases, so-called penetration enhancers have to be used. They reduce the barrier function of the skin and thus increase the maximum active substance flow.

Most of these penetration enhancers are liquid at room temperature and frequently have to be released to the skin at relatively high quantities. The same inevitable problem as in the case of active substances arises. At high concentrations, these substances have an intolerable negative effect on the cohesion of the matrix.

If the active substance, for example, belongs to the group of the antirheumatics, the patches have to be rather large due to the relatively high active substance doses required. For most active substances of this group the size of the patches must at least amount to 100 cm$^2$. For reasons of convenience, non-elastic films cannot be used as backing layer in such large patches. Textile fabrics are recommended in this case. Since such patches are preferably worn for several days, it is advantageous to render them water-repellent but permeable to water vapor. The water-repellency prevents the plaster from being soaked with water when having a shower, and the permeability to water vapor lessens the occlusive effect. In addition, such patches advantageously contain a component which locally stimulates the blood stream or creates a feeling of warmth. Many of these substances, e.g., nicotinates and methyl salicylates, are liquid at room temperature and thus increase the consistency problem.

The problems with respect to consistency are particularly severe in the so-called bag or pouch systems which contain the active substance in a liquid or semi-liquid preparation. These systems have the form of a bag which represents the active substance reservoir and is formed by an impermeable backing layer and a membrane. In most cases, the membrane controls the release of active substances and/or adjuvants from the system. The membrane is provided with a thin adhesive layer in order to anchor the system to the skin. Said adhesive layer gets saturated up to an equilibrium with all ingredients capable of diffusion and thus also with the liquid components of the active substance reservoir resulting in the respective consequences with respect to consistency of the adhesive.

Compared to the active substances, most of the penetration enhancers consist of relatively small molecules and exhibit a high diffusion velocity in the matrix. For this reason, the matrix could be made thicker to increase its absorption capacity for penetration enhancers at the same concentration level. However, this solution of the problem entails the disadvantage that larger amounts of active substances, which frequently are very expensive, have to be employed since the concentration of active substance cannot be lowered without thereby adversely affecting the active substance flow.

Another possibility is described in U.S. Pat. No. 4,746,515 (Alza). In this case, the matrix consists of two layers, whereby the layer remote from the skin exclusively contains penetration enhancers. However, this solution can only be applied, if the active substance within the layer which is closer to the skin is present above the saturation solubility, i.e., in a partially crystalline form. Otherwise, a concentration compensation between both matrix layers would take place.

If the active substance itself is the softening component, this solution is out of question. In this case, an adequate consistency of the matrix has to be achieved by a suitable formulation. In case of adhesives based on polyisobutylene or styrene-butadiene-block copolymers, for example, a different mixture of the basic polymer with the tackifying additives can lessen the softening effects.

In case of the polyacrylates or polysiloxanes, respectively, the consistency of the matrix can in principle be improved by a different molecular weight distribution within the adhesive. However, this involves that a new adhesive has to be synthesized and that well-proven adhesive formulations available on the market, which are toxicologically examined, cannot be used. A further possibility is to chemically modify the glues in a later stage, e.g., by an additional chemical cross-linkage of the polymer molecules. Strictly speaking, however, this only influences the molecular weight distribution, too.

This method is described by the international patent application No. WO 80814 (Key Pharmaceuticals, Inc.). It is emphasized therein that such a subsequent cross-linkage eliminates the tackiness of a polyacrylate adhesive; however, the combination with the softening active substance (in this particular case it is nitroglycerine), which is incorporated in high concentrations, results in sufficient tackiness with good cohesion effected by said cross-linking. However, this solution entails the disadvantage that reactive substances, the physiological acceptability of which has to be ensured, are mixed to the adhesive.

Physiologically acceptable metal chelates (e.g., titanium-acetylacetonate, aluminum-acetylacetonate), which provide a certain subsequent cross-linkage of the adhesive after removal of the solvent, are mixed to many polyacrylate-based adhesives which are suitable for medical purposes. This subsequent cross-linkage is effected to obtain adhesive solutions having a low viscosity and a high solids content.

However, the degree of such a subsequent cross-linkage is directed to an adhesive without additional softeners; it cannot be increased at will, even if the metal chelate content is increased. The action of active substances and/or correctives can therefore only be compensated within certain limits.

It was accordingly the object of the present invention to find a solution for this consistency problem occurring ring in case of high concentrations of softening active substances and/or softening adjuvants, such as penetration accelerators, without having to synthesize a new, special polyacrylate adhesive or having to subject a polyacrylate which by itself exhibits optimum adhesive properties to a subsequent chemical modification. Consequently, the scope of application of commercially available polyacrylate adhesives which possibly are already used in other medical products should be enlarged.

Most surprisingly, this object was achieved by adding a polymer to the polyacrylate-based adhesive. Said polymer is no adhesive by itself but it exhibits very good film-forming properties.

Thus, the subject matter of the present invention is a device for the topical and systemic administration of active substances to or through the skin consisting of a backing layer, at least one self-adhesive layer, and a removable protective layer, wherein the self-adhesive layer consists of
  (a) 100 parts by weight of a polyacrylate adhesive,
  (b) 5 to 150, preferably 10 to 100, and in particular preferred 15 to 50 parts by weight of a film-former compatible with polyacrylates,
  (c) 0 to 250 parts by weight of a non-softening active substance and/or adjuvant, and
  (d) 10 to 250 parts by weight of a softening active substance and/or adjuvant.

Due to the high molecular weight, the film-forming polymer positively influences the cohesion of the matrix and renders it extremely absorptive to softening ingredients. In case of a sufficient amount of film-forming polymer, softening active substances and/or penetration enhancers may be incorporated to an amount of up to 50%-wt. Film-forming polymers based on polyacrylates or polymethacrylates have proven to be very suitable. Particularly suitable are copolymers of methyl methacrylate and butyl methacrylate having an average molecular weight of approximately 200,000. Such polymethacrylates are used, for example, in so-called spray plasters, i.e., they are dissolved in a physiologically acceptable solvent, directly sprayed on the skin or open wound from the spray bottle by means of a propellant, and—after evaporation of the solvent—form a film adhering to the skin.

An additional advantage of said film-forming polymers is their poor interaction with active substances and/or auxiliary agents so that they do not have any negative effects on the release rate of these substances.

If the adhesive force of the matrix is too reduced due to the high content of film-forming polymer, this can effectively be corrected by adding approximately 5 to 15% of a strongly tackifying resin.

Any resins compatible with polyacrylates may be used as additional, tackifying additives. In this connection, phthalic esters of hydroabietyl alcohol, glycerol esters of hydrogenated colophony and low-molecular polyacrylates have proved to be particularly suitable.

Examples of softening adjuvants are penetration enhancers and solubilizers. Their choice is mainly determined by the nature of the active substance. Examples of proven penetration accelerators include fatty alcohols, fatty acid esters, propylene glycol, oleic acid, glycerol derivatives, dioctyl cyclohexane, N-methylpyrrolidone, or caprolactam derivatives. Propylene glycol, glycerol, polyethylene glycol, ethanol, ethyl acetate, or acetoacetic ester are examples of suitable solubilizers.

Pigments, such as titanium oxide and zinc oxide, active substance carriers, such as lactose and silica gel, antioxidants, separating agents, such as talc, buffering substances, such as inorganic salts, glycine and leucine, and water absorbers are of first consideration within the group of non-softening adjuvants.

In general, a single-layer structure of the reservoir will meet the demands, however, special requirements, e.g., adjustment of a concentration gradient of active substance and/or auxiliary agent, may require a multilayer composition.

If the reservoir is of a liquid or semisolid consistency, a preferred embodiment of the device according to the present invention is the so-called bag system described hereinabove.

For all other components of the device, the simplest design of which merely consists of a backing layer and a removable protective layer, in principle all materials can be used which are employed for this purpose in ordinary patches, topical and transdermal systems directed to the same application.

If the release of active substances and/or adjuvants has to be controlled by a membrane, this membrane is an integral part of the reservoir layer. Examples of materials suitable for the use as backing layers include flexible or inflexible films of polyethylene, polypropylene, polyethylene terephthalate, polyvinyl chloride, polyurethane, ethylene-vinyl-acetate-copolymers, or polyamide.

Frequently, the desired properties can only be achieved by using laminates of the above mentioned materials.

Metal foils, e.g., aluminum foil or paper, alone or coated with a polymeric material, may also be used. Textile fabrics may be employed too, if the components of the reservoir may not escape therefrom via the gas phase due to their physical data.

Except for textile fabrics, the same materials can in principle be used for the removable protective foil, however, they must additionally be rendered adhesive. Said adhesive finish may be achieved by a special silicone treatment.

Examples of active substances which can be administered by the device according to the present invention include coronary stimulants, such as molsidomine, nitroglycerin, isosorbide mononitrate and isosorbide dinitrate, $\alpha$1-receptor-blockers, such as prazosine and terazosine, $\beta$-blockers, such as betaxolol, pindolol, timolol, carteolol and carazolol, calcium antagonists, such as nifedipine and verapamil, antiphlogistics and non-steoridal antirheumatics, such as etofenamate, indometacin, piroxicam, acemetacin, diclofenac, ibuprofen, flurbiprofen, ketoprofen, carprofen, as well as salicylic acid derivatives, such as ethylene glycol monosalicylate, methyl salicylate, salicylamide, or phenyl salicylate, analgesics, such as morphine, dihydrocodeine, hydromorphone, dihydrohydroxycodeinone or levomethadone, and hormones, such as estradiol, levonorgestrel, norethisterone acetate, testosterone, and 19-nortestosterone.

According to the present invention, therapeutically expedient combinations of active substances can also be employed.

For instance, in the treatment of rheumatic diseases a local stimulation of the blood flow or creation of a feeling of warmth at the place of the body to be treated is desirable. For this purpose, agents stimulating the blood flow which create a local feeling of warmth (rubefacients, such as nonivamide (pelargonic acid vanillylamide), capsaicin, nicotinic acid derivatives, such as benzyl nicotinates, methyl nicotinates, pyridyl-3-carbinol and the salts thereof) may be added to the patches according to the present invention.

The present invention will be illustrated by the following examples.

EXAMPLES

1. Patch with nitroglycerin as active substance 193 g polyacrylate-based adhesive solution (Durotak 2280-2287 [National Starch], 45% in ethyl acetate)
31.9 g film-forming polyacrylate, copolymer of methacrylic methylester and methacrylic butylester, e.g., Plastoid B (Rbhm-Pharma)
450 g nitroglycerin solution (5% in chloroform)
21 g aluminum-acetylacetonate solution (4% in ethyl acetate) are mixed and homogenized. The liquid mass is spread at a thickness of 350 μm on two films of different siliconization degree; the mass is dried at 500° C. over a 15-minute period. The dry films are laminated on top of each other; the stronger siliconized film is removed. The laminate is covered, e.g., with a polyester film. The matrix of the transdermal system so produced has an area weight of 160 g/m$^2$ and a content of liquid nitroglycerine of 15%-wt. 1.3 mg nitroglycerin were released per cm$^2$ and 24 hours under in vitro conditions.

This release rate suffices for therapeutic purposes.

2. Patch with etofenamate as active substance

Etofenamate is an oily liquid at room temperature
125 g polyacrylate adhesive solution (Durotak 2280-2287 (National Starch), 45% in ethyl acetate)
125 g film-forming polyacrylate, copolymer of methacrylic methylester and methacrylic butylester (50% w/w in ethyl acetate) Plastoid B (Röhm-Pharma)
90 g Etofenamate
3 g aluminum-acetylacetonate solution (4% in ethyl acetate)
are mixed and homogenized. The liquid mass is spread at a thickness of 200 μm on siliconized films and dried for 20 minutes at 500° C. The dry film is then covered with a polyester film or a textile carrier fabric. The matrix of the transdermal system thus prepared has an area weight of 90 g/m$^2$ and a content of liquid etofenamate of 44%-wt. 0.2 mg Etofenamate were released per cm$^2$ and 24 hours under in vitro conditions. This release rate is rapid enough for therapeutic purposes.

3. Patch with Ethylene Glycol Monosalicylate 128 g copolymer of methacrylic methylester and methacrylic butylester (50% w/w in ethyl acetate) e.g., Plastoid B (Rbhm Pharma)
282 g polyacrylate adhesive (50% w/w in ethyl acetate), e.g., Durotak 126-1050 (National Starch)
59 g glycerol ester of hydrogenated colophony (50% in ethyl acetate) e.g., Staybelite Ester 5E (Hercules)
18 g dioctyl cyclohexane, e.g., Cetiol S (Henkel)
45 g ethylene glycol monosalicylate
7.5 g pelargonic acid vanillylamide
20.2 g aluminum-acetylacetonate (4.2% w/w in ethyl acetate)
are mixed and homogenized. Next, a film is spread on films having a different degree of siliconization; after drying for 25 minutes at 500C, the film has an area weight of 150 g/m$^2$. The two adhesive films are laminated on top of each other; the stronger siliconized film is removed and replaced by a textile carrier. The finished patches are obtained by punching or cutting, respectively.

4. Patch with Ethylene Glycol Monosalicylate and Benzyl Nicotinate as Warming Component 118 g film-former based on poly(ethyl acrylate, methyl methacrylate, trimethylammonioethyl methacrylate chloride) e.g., Eudragit RL (Röhm Pharma)
290 g polyacrylate adhesive (50% w/w in ethyl acetate) e.g., Durotak 280-2287 (National Starch)
30 g ethylene glycol monosalicylate
3 g benzyl nicotinate
10 g titanium-acetylacetonate (10% w/w in 2-propanol)
are mixed and homogenized. Next, two foils of a different siliconization degree are spread with a film of this mass; after drying for 25 minutes at 500° C., an area weight of 150 g/m$^2$ results. The two adhesive films are laminated on top of each other, the stronger siliconized film is removed and replaced by a textile carrier. The finished patches are obtained by punching or cutting.

5. Plaster Formulations having a High Content of Liquid Penetration Enhancers or Softening Additives, respectively The following general formulation may be used, if plaster formulations are required in which high concentrations of softening active substances and/or softening penetration enhancers are needed.

100 g polyacrylate adhesive solution (Durotak 2280-2287 (National Starch), 50% in ethyl acetate)
X g solution of a film-forming polyacrylate (Plastoid B (Röhm Pharma), 50% in ethyl acetate)
10 g aluminum-acetylacetonate solution (4% in ethyl acetate)
Y g softening penetration enhancer or adjuvant, respectively
are mixed and homogenized. The liquid mass is spread at a thickness of 250 μ on siliconized films, followed by drying for 20 minutes at 500° C. They are then covered with a suitable film.

5.a to 5.e are examples prepared according to the formulation as described under 5. The active substances are not indicated, however, adequate amounts thereof may be added to all formulations.

| Penetration enhancer Softener | Content in matrix after removal of solvent |
| --- | --- |
| 5a. n-dodecanol<br>X = 29.7; Y = 16 | 20% |
| 5b. oleic acid<br>X = 32; Y = 16 | 20% |
| 5c. propylene glycol<br>X = 32; Y = 16 | 20% |
| 5d. propylene glycol<br>X = 16; Y = 32 | 33% |
| 5e. N-methylpyrrolidone<br>X = 16; Y = 32 | 33% |

It is understood that the specification and examples are illustrative but not limitative of the present invention and that other embodiments within the spirit and scope of the invention will suggest themselves to those skilled in the art.

We claim:

1. A device for the topical and systemic administration of an active substance to or through the skin comprising a backing layer, at least one self-adhesive layer, and a removable protective layer, the self-adhesive layer comprising
   (a) 100 parts by weight of a polyacrylate adhesive,
   (b) 5 to 150 parts by weight of a film-former compatible with polyacrylates, said film-former being based on at least one of a polyacrylate and polymethacrylate,
   (c) 0 to 250 parts by weight of at least one of a non-softening active substance and an adjuvant selected from the group consisting of pigments, active substance carriers, antioxidants, separating agents, buffering substances, water absorbers and combinations thereof, and
   (d) 10 to 250 parts by weight of at least one member selected from the group consisting of a softening active substance, a tackifying additive, a softening adjuvant, and an adjuvant or active substance which locally stimulates the blood flow or creates a feeling of warmth, where the substance is at least one of an antiphlogistic and an antirheumatic.

2. The device according to claim 1 wherein the film-former is a polyacrylate.

3. The device according to claim 1 wherein component (d) of the self-adhesive layer additionally comprises a tackifying resin selected from the group consisting of a phthalic ester of hydroabiethyl alcohol, a glycerol ester of hydrogenated colophony, and a low-molecular polyacrylate.

4. The device according to claim 1 containing as the or an adjuvant of component (d) a penetration enhancer.

5. The device according to claim 1 wherein the active substance is nitroglycerin.

6. The device according to claim 1 wherein the active substance is a calcium antagonist.

7. The device according to claim 1 wherein the active substance is at least one of antiphlogistic and an antirheumatic.

8. The device according to claim 7 wherein the active substance is a salicylate.

9. The device according to claim 8 wherein the salicylate is ethylene glycol monosalicylate.

10. The device according to claim 7 wherein the active substance is etofenamate.

11. The device according to claim 7 wherein the active substance is indometacin.

12. The device according to claim 7 wherein the active substance is ibuprofen.

13. The device according to claim 7 wherein the active substance is piroxicam.

14. The device according to claim 7 wherein the self-adhesive layer contains an adjuvant or active substance which locally stimulates the blood flow or creates a feeling of warmth.

15. The device according to claim 14 wherein said adjuvant or active substance is pelargonic acid vanillylamide.

16. The device according to claim 14 wherein said adjuvant or active substance is benzyl nicotinate.

17. The device according to claim 7 wherein the backing layer is a textile fabric.

18. The device according to claim 17 wherein the textile fabric is water-repellent.

19. The device according to claim 17 wherein the textile fabric is permeable to water vapor.

20. The device according to claim 1 wherein the active substance is an analgesic.

21. The device according to claim 1 wherein the active substance is a hormone.

22. The device according to claim 1 wherein the active substance is a coronary stimulant.

23. The device according to claim 1 wherein the active substance is a beta-blocker.

24. The device according to claim 1 wherein the system is a matrix system.

25. The device according to claim 24 wherein the matrix layer has a multi-layer structure.

26. The device according to claim 25 including a membrane controlling the release of active substance or adjuvants.

27. The device according to claim 1 wherein the system is a bag system comprising the active substance in a substantially liquid or semisolid preparation.

28. The device according to claim 1 wherein the film-former of component (b) is present in an amount of from 10 to 100 parts by weight.

29. The device according to claim 28 wherein the amount is in the range of from 15 to 50 parts by weight.

30. The device according to claim 1 wherein the film-former by itself is not adhesive.

31. The device according to claim 2 wherein the film-former is a polymethacrylate or a copolymer of methylmethacrylate and butylmethacrylate.

32. The device according to claim 3 wherein the amount of the tackifying resin in is in the range of from 5 to 15%.

33. The device according to claim 1 wherein the total amount of the softening active substance of component (d), a penetration enhancer and a combination thereof is up to 50% by weight.

34. The device according to claim 33 wherein the calcium antagonist is verapamil.

* * * * *